(12) United States Patent
Frampton et al.

(10) Patent No.: US 11,389,225 B2
(45) Date of Patent: Jul. 19, 2022

(54) SMOKE EVACUATION DEVICE REMOTE ACTIVATION SYSTEM

(71) Applicant: Megadyne Medical Products, Inc., Draper, UT (US)

(72) Inventors: Chad S. Frampton, American Fork, UT (US); Jason L. Harris, Lebanon, OH (US); Frederick Shelton, Hillsboro, OH (US); David C. Yates, West Chester, OH (US)

(73) Assignee: Megadyne Medical Products, Inc., Draper, UT (US)

( * ) Notice: Subject to any disclaimer, the term of this patent is extended or adjusted under 35 U.S.C. 154(b) by 1098 days.

(21) Appl. No.: 15/826,289

(22) Filed: Nov. 29, 2017

(65) Prior Publication Data
US 2019/0159825 A1    May 30, 2019

(51) Int. Cl.
*A61B 18/16*    (2006.01)
*A61B 18/12*    (2006.01)
(Continued)

(52) U.S. Cl.
CPC ...... *A61B 18/1233* (2013.01); *A61B 18/1402* (2013.01); *A61B 18/16* (2013.01);
(Continued)

(58) Field of Classification Search
CPC .......... A61B 18/1233; A61B 2218/008; A61B 2018/00178; A61B 2018/00642; A61B 2018/00827
See application file for complete search history.

(56) References Cited

U.S. PATENT DOCUMENTS

| 1,165,288 A | 12/1915 | Rimmer |
| 1,789,194 A | 1/1931 | Rockwell |

(Continued)

FOREIGN PATENT DOCUMENTS

| CN | 304909540 S | 11/2018 |
| WO | 9408698 | 4/1994 |

(Continued)

OTHER PUBLICATIONS

Chinese Patetn Application No. 201830176822, filed on Apr. 2018.
(Continued)

*Primary Examiner* — Linda C Dvorak
*Assistant Examiner* — Ryan T Clark
(74) *Attorney, Agent, or Firm* — Workman Nydegger

(57) ABSTRACT

A radio frequency (RF) current sensor for remotely activating a smoke evacuation device in an electrosurgical system includes a sensor body with a cable interfacing sidewall and a retaining member. The cable interfacing sidewall and the retaining member define a retention pocket for receiving a cable communicating RF current. The RF current sensor additionally includes a sensor element for detecting RF current in the cable and a sensor cable in electrical communication with the sensor element. The RF current sensor can operate in at least two modes, depending on whether the cable communicates RF current to a monopolar or bipolar electrosurgical instrument, but regardless of the operation mode, the sensor cable can communicate an activation signal and a current signal derived from the detected RF current to the smoke evacuation device, which activates or adjusts the period of time and/or the smoke evacuation flow rate of a vacuum source.

20 Claims, 6 Drawing Sheets

(51) Int. Cl.
*A61B 18/14* (2006.01)
*A61B 18/00* (2006.01)

(52) U.S. Cl.
CPC .............. *A61B 2018/00178* (2013.01); *A61B 2018/00589* (2013.01); *A61B 2018/00595* (2013.01); *A61B 2018/00601* (2013.01); *A61B 2018/00642* (2013.01); *A61B 2018/00702* (2013.01); *A61B 2018/00732* (2013.01); *A61B 2018/00744* (2013.01); *A61B 2018/00827* (2013.01); *A61B 2218/006* (2013.01); *A61B 2218/008* (2013.01)

(56) References Cited

U.S. PATENT DOCUMENTS

| | | |
|---|---|---|
| 2,577,606 A | 12/1951 | Conley |
| 3,815,752 A | 6/1974 | Hoffman et al. |
| 3,841,490 A | 10/1974 | Hoffman et al. |
| 4,157,234 A | 6/1979 | Shaffer et al. |
| 4,396,206 A | 8/1983 | Tsuge et al. |
| 4,619,672 A | 10/1986 | Robertson |
| D291,353 S | 8/1987 | Conero |
| 4,701,193 A | 10/1987 | Robertson et al. |
| 4,786,298 A | 11/1988 | Billet et al. |
| 4,810,269 A | 3/1989 | Stackhouse et al. |
| 4,826,513 A | 5/1989 | Stackhouse et al. |
| 4,986,839 A | 1/1991 | Wertz et al. |
| D315,410 S | 3/1991 | Aten |
| 5,108,389 A | 4/1992 | Comescu |
| 5,144,176 A | 9/1992 | Popper |
| 5,160,334 A | 11/1992 | Billings et al. |
| 5,221,192 A | 6/1993 | Heflin et al. |
| 5,226,939 A | 7/1993 | Nicolas et al. |
| 5,242,474 A | 9/1993 | Herbst et al. |
| 5,288,469 A | 2/1994 | Skalla et al. |
| 5,318,516 A | 6/1994 | Comescu |
| 5,336,218 A | 8/1994 | Linhares |
| 5,342,349 A | 8/1994 | Kaufman |
| 5,423,779 A | 6/1995 | Yeh |
| 5,431,650 A | 7/1995 | Comescu |
| 5,522,808 A | 6/1996 | Skalla |
| 5,597,385 A | 1/1997 | Moerke |
| 5,619,992 A * | 4/1997 | Guthrie .............. A61B 5/14552 356/41 |
| 5,620,441 A * | 4/1997 | Greff ...................... A61B 18/00 604/35 |
| 5,674,219 A | 10/1997 | Monson et al. |
| 5,690,480 A | 11/1997 | Suzuki et al. |
| 5,853,410 A | 12/1998 | Greff et al. |
| 5,874,052 A | 2/1999 | Holland |
| 5,910,291 A | 6/1999 | Skalla et al. |
| 5,992,413 A | 11/1999 | Martin et al. |
| D420,140 S | 2/2000 | Mobile |
| 6,050,792 A | 4/2000 | Shaffer |
| 6,089,527 A | 7/2000 | Utterberg |
| 6,110,259 A | 8/2000 | Schultz et al. |
| 6,129,530 A | 10/2000 | Shaffer |
| 6,145,509 A | 11/2000 | Tanner |
| 6,203,762 B1 | 3/2001 | Skalla et al. |
| 6,439,864 B1 | 8/2002 | Shaffer |
| 6,511,308 B2 | 1/2003 | Shaffer |
| 6,524,307 B1 | 2/2003 | Palmerton et al. |
| 6,544,210 B1 | 4/2003 | Trudel et al. |
| 6,585,791 B1 | 7/2003 | Garito et al. |
| 6,589,316 B1 | 7/2003 | Schultz et al. |
| 6,592,543 B1 | 7/2003 | Wortrich et al. |
| 6,616,722 B1 | 9/2003 | Cartellone |
| 6,663,698 B2 | 12/2003 | Mishin et al. |
| 6,709,248 B2 | 3/2004 | Fujioka et al. |
| 6,736,620 B2 | 5/2004 | Satoh |
| 6,758,885 B2 | 7/2004 | Leffel et al. |
| 6,786,707 B2 | 9/2004 | Kim |
| 7,014,434 B2 | 3/2006 | Fujioka et al. |
| 7,258,712 B2 | 8/2007 | Schultz et al. |
| 7,276,052 B2 | 10/2007 | Kobayashi et al. |
| 7,294,116 B1 | 11/2007 | Ellman et al. |
| D568,991 S | 5/2008 | Schwikert |
| 7,465,156 B2 | 12/2008 | Lee |
| 7,497,340 B2 | 3/2009 | Hershberger et al. |
| D608,447 S | 1/2010 | Meyer |
| 7,819,957 B2 | 10/2010 | Roberts et al. |
| 7,942,655 B2 | 5/2011 | Shaffer |
| 8,033,798 B2 | 10/2011 | Suh et al. |
| 8,142,175 B2 | 3/2012 | Duppert et al. |
| D657,468 S | 4/2012 | Held |
| 8,190,398 B2 | 5/2012 | Kitaguchi et al. |
| 8,298,420 B2 | 10/2012 | Burrows |
| 8,608,816 B2 | 12/2013 | Palmerton et al. |
| 8,684,705 B2 | 4/2014 | Magoon et al. |
| 8,727,744 B2 | 5/2014 | Magoon et al. |
| 9,011,366 B2 | 4/2015 | Dean et al. |
| 9,028,230 B2 | 5/2015 | Shaffer |
| 9,067,030 B2 | 6/2015 | Stearns et al. |
| 9,074,598 B2 | 7/2015 | Shaffer et al. |
| D739,770 S | 9/2015 | Scampoli |
| 9,199,047 B2 | 12/2015 | Stearns et al. |
| 9,215,964 B2 | 12/2015 | Loske |
| 9,366,254 B2 | 6/2016 | Murakami |
| 9,387,295 B1 | 7/2016 | Mastri et al. |
| 9,387,296 B1 | 7/2016 | Mastri et al. |
| 9,415,160 B2 | 8/2016 | Bonano et al. |
| 9,435,339 B2 | 9/2016 | Calhoun et al. |
| 9,474,512 B2 | 10/2016 | Blackhurst et al. |
| 9,549,849 B2 | 1/2017 | Charles |
| 9,579,428 B1 | 2/2017 | Reasoner et al. |
| D799,055 S | 10/2017 | Kennedy |
| D868,287 S | 11/2019 | Frampton |
| 2004/0223859 A1 | 11/2004 | Sharp |
| 2005/0000196 A1 | 1/2005 | Schultz |
| 2005/0189283 A1 | 9/2005 | Smit et al. |
| 2006/0099096 A1 | 5/2006 | Shaffer et al. |
| 2006/0224150 A1 * | 10/2006 | Arts ........ A61B 18/16 606/32 |
| 2007/0066970 A1 | 3/2007 | Ineson |
| 2009/0022613 A1 | 1/2009 | Dai et al. |
| 2014/0356207 A1 | 12/2014 | Yang |
| 2015/0133750 A1 * | 5/2015 | White .................. A61B 5/4337 600/306 |
| 2015/0224237 A1 | 8/2015 | Reasoner et al. |
| 2015/0273381 A1 | 10/2015 | Stoner et al. |
| 2016/0000494 A1 | 1/2016 | Comescu |
| 2016/0001102 A1 | 1/2016 | Huh |
| 2016/0169941 A1 * | 6/2016 | Fukui .................. G01R 15/207 324/117 R |
| 2016/0287817 A1 | 10/2016 | Mastri et al. |
| 2016/0367266 A1 | 12/2016 | Palmerton et al. |
| 2017/0014557 A1 | 1/2017 | Minskoff et al. |
| 2017/0165725 A1 | 6/2017 | Hersey et al. |
| 2017/0181768 A1 | 6/2017 | Galley |
| 2019/0159830 A1 | 5/2019 | Horner et al. |

FOREIGN PATENT DOCUMENTS

| | | |
|---|---|---|
| WO | 2016142690 | 9/2016 |
| WO | 201703712 | 1/2017 |
| WO | 2017112684 | 6/2017 |

OTHER PUBLICATIONS

International Search and Written Opinion for PCT/IB2018/059371 dated Feb. 15, 2019.

Non-Final Office Action for U.S. Appl. No. 29/627,788 dated Feb. 19, 2019.

Notice of Allowance for U.S. Appl. No. 29/627,788 dated Jul. 23, 2019.

* cited by examiner

SMOKE EVACUATION DEVICE REMOTE ACTIVATION SYSTEM

BACKGROUND

Technical Field

The present disclosure relates to smoke evacuation devices used in electrosurgical systems. More specifically, the present disclosure relates to apparatus and methods of controlling flow parameters of a smoke evacuation device.

The Relevant Technology

As is known to those skilled in the art, modern surgical techniques typically employ radio frequency (RF) power to cut tissue and coagulate bleeding encountered in performing surgical procedures. This type of surgery is known as electrosurgery. Electrosurgery is widely used and offers many advantages, including the use of a single surgical instrument for both cutting and coagulating tissue. A monopolar electrosurgical generator system has an active electrode, such as in the form of an electrosurgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue through cauterization. The return electrode carries the same RF signal provided to the electrode or tip of the electrosurgical instrument, after it passes through the patient, thus providing a path back to the electrosurgical generator.

Electrosurgical instruments communicate electrical energy to a target tissue of a patient to cut the tissue and/or cauterize blood vessels within and/or near the target tissue. This cauterization results in smoke released into the air that can be unpleasant, obstructive of the view of a practitioner. Many electrosurgical systems may therefore employ an evacuation system that captures the resulting smoke and directs it through a filter and exhaust port, away from practitioners and/or patients. A smoke evacuation device typically creates suction directed at the smoke using fans to draw the smoke through a tube connecting the surgical instrument to an exhaust port.

Smoke evacuation devices often use filters in order to remove unwanted pollutants from the smoke exhaust before the air is released from the exhaust port. Periodically replacing filters is necessary for the smoke evacuation device to remain effective, and increasing the life span of filters is desirable.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

The present disclosure relates to electrosurgical systems. More specifically, the present disclosure relates to radio frequency (RF) current sensors for remotely activating smoke evacuation devices within an electrosurgical system, to methods for remotely activating smoke evacuation devices, and to electrosurgical systems employing RF current sensors for remotely activating smoke evacuation devices. Smoke evacuation devices are inefficiently and statically operated, causing, at the very least, a reduction in the life span of associated smoke filters. The RF current sensors, methods for remotely activating smoke evacuation devices, and electrosurgical systems employing RF current sensors for remotely activating smoke evacuation devices of the present disclosure enable activation and dynamic operation of smoke evacuation devices, thereby increasing the efficiency and life span of smoke evacuation devices and components thereof.

In an embodiment, an RF current sensor is configured to operate in at least two modes—a first mode and a second mode—and includes (i) a sensor body having at least a cable interfacing sidewall and a retaining member, the cable interfacing sidewall and the retaining member defining a retention pocket configured to receive a cable communicating RF current, (ii) a sensor element for detecting RF current in the cable, and (iii) a sensor cable in electrical communication with the sensor element, the sensor cable communicating one or more of an activation signal or a current signal derived from the detected RF current to the smoke evacuation device.

The RF sensor can operate in the first mode when the sensor element identifies a single RF current in the cable. The single RF current in the cable can be communicated between a signal generator and an active electrode of a monopolar electrosurgical instrument or between a return electrode and the signal generator, and the activation signal and/or the current signal are derived from the single RF current when the RF current sensor operates in the first mode. The RF sensor can operate in the second mode when the sensor element identifies two RF currents—a first RF current flowing in an opposite direction as a second RF current—in the cable. Operating in the second mode causes the RF current sensor to detect the first RF current with respect to the second RF current and to derive the activation signal and/or the current signal from the first RF current.

In an embodiment, a method for remote activation of a smoke evacuation device includes (i) generating an RF current at a signal generator, (ii) communicating the RF current through a source cable to an electrosurgical instrument, (iii) detecting an activation of RF current with an RF current sensor communicatively coupled to a smoke evacuation device, (iv) communicating an activation signal from the RF current sensor to the smoke evacuation device in response to detecting the activation of RF current, (v) receiving the activation signal at the smoke evacuation device, and (vi) activating a vacuum source for one or more of a defined period of time or to generate a defined smoke evacuation flow rate in response to receiving the activation signal.

In some embodiments, the method for remote activation of a smoke evacuation device can additionally include (i) detecting the RF current with the RF current sensor subsequent to detecting the activation of RF current, (ii) periodically or continuously communicating a current signal from the RF current sensor to the smoke evacuation device in response to detecting the RF current, the signal current including data associated with the RF current, (iii) receiving the current signal at the smoke evacuation device, and (iv) in response to receiving the current signal, adjusting the defined period of time and/or the defined smoke evacuation flow rate of the vacuum source.

In some embodiments, the method for remote activation of a smoke evacuation device can additionally include deriving a treatment power based on the activation signal and/or the current signal and calculating an estimated smoke production based on the treatment power, and the defined period of time and/or the defined smoke evacuation flow rate can be based on the estimated smoke production.

In an embodiment, an electrosurgical system includes (i) a signal generator producing an RF current, (ii) a source cable electrically coupled to the signal generator and to an electrosurgical instrument, the source cable communicating the RF current from the signal generator to the electrosurgical instrument, (iii) a smoke evacuation device that includes a vacuum hose positioned proximate the electrosurgical instrument and configured to evacuate smoke generated by the electrosurgical instrument, and (iv) an RF current sensor communicatively coupled to the smoke evacuation device, the RF current sensor activating the smoke evacuation device in response to identifying the RF current.

In some embodiments, the RF current sensor is removably coupled to the source cable or the return cable and detects RF current flowing therethrough. In some embodiments, the RF current sensor is integrally formed within the return electrode or within the smoke evacuation device.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Additional features and advantages of the disclosed embodiments will be set forth in the description which follows, and in part will be obvious from the description, or may be learned by the practice of the disclosure. These and other features will become more fully apparent from the following description and appended claims, or may be learned by the practice of the present disclosure.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

Figure 1:
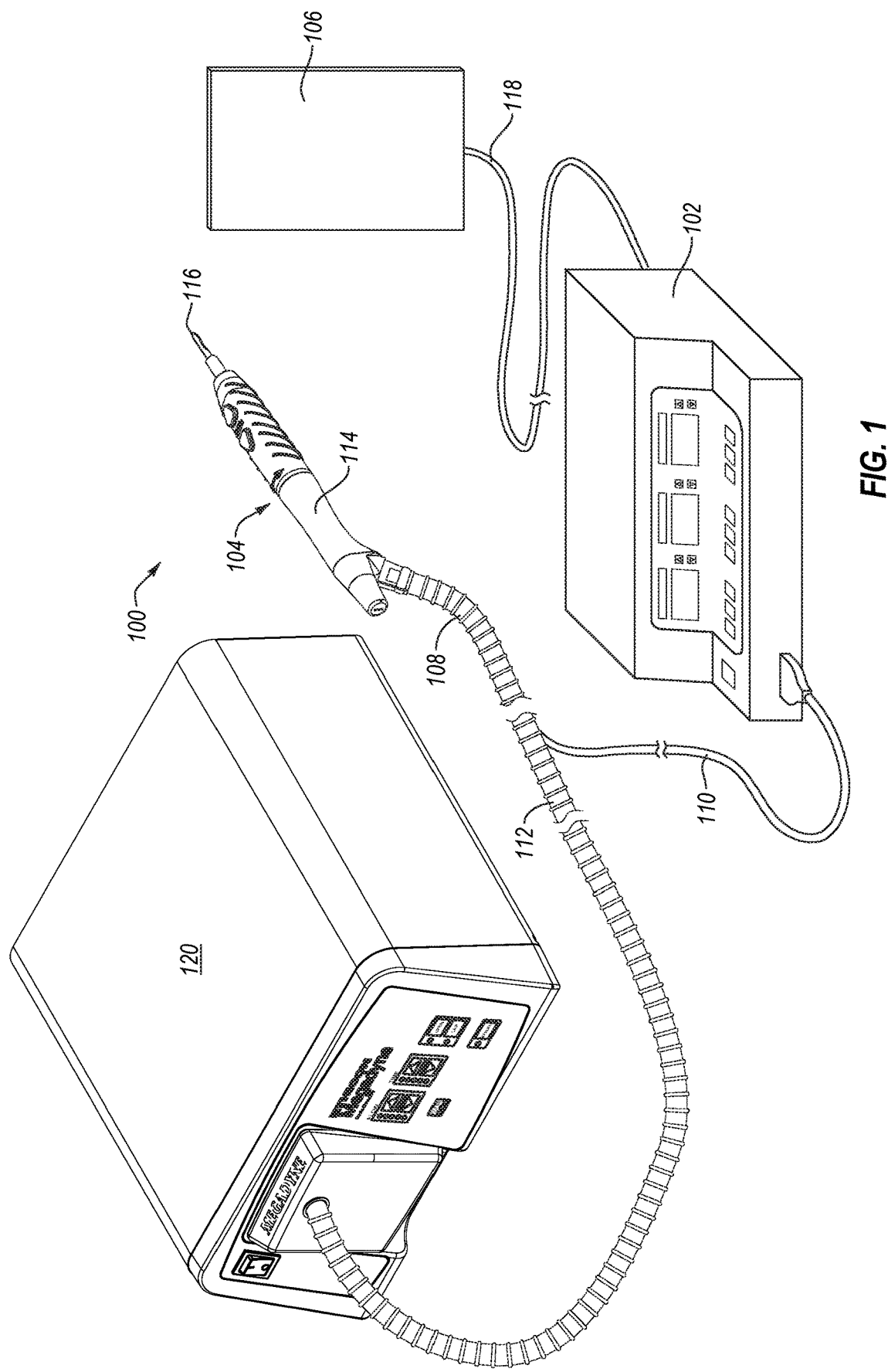
FIG. 1 illustrates an exemplary electrosurgical system.

The present disclosure relates to smoke evacuation devices associated with electrosurgical instruments and other hand-held instruments that produce smoke or cause smoke to be produced during use. FIG. 1, for example, illustrates an exemplary electrosurgical system 100. The illustrated embodiment includes a signal generator 102, an electrosurgical instrument 104, and a return electrode 106. Generator 102, in one embodiment, is an RF wave generator that produces RF electrical energy. Connected to electrosurgical instrument 104 is a utility conduit 108. In the illustrated embodiment, utility conduit 108 includes a cable 110 that communicates electrical energy from generator 102 to electrosurgical instrument 104. The illustrated utility conduit 108 also includes a vacuum hose 112 that conveys captured/collected smoke and/or fluid away from a surgical site and to, for example, a smoke evacuation device 120. In some embodiments, such as that illustrated in FIG. 1, cable 110 can extend through at least a portion of vacuum hose 112 and to electrosurgical instrument 104.

Generally, electrosurgical instrument 104 includes a hand piece or pencil 114 and an electrode tip 116. Electrosurgical instrument 104 communicates electrical energy to a target tissue of a patient to cut the tissue and/or cauterize blood vessels within and/or near the target tissue. Specifically, an electrical discharge is delivered from electrode tip 116 to the patient in order to cause heating of cellular matter of the patient that is in close contact with electrode tip 116. The heating takes place at an appropriately high temperature to allow electrosurgical instrument 104 to be used to perform electrosurgery. Return electrode 106 is connected to generator 102 by a cable 118 in order to complete the circuit and provide a return electrical path to wave generator 102 for energy that passes into the patient's body.

As explained in greater detail below, embodiments of electrosurgical systems according to the present disclosure enable efficient activation and dynamic capture of smoke generated during an electrosurgical procedure. For example, vacuum suction originating from the smoke evacuation device 120 can be activated and/or adjusted by a sensor that detects activation of RF current and turns on the vacuum suction in response to detecting activation of RF current and that monitors the RF current, adjusting the flow rate and/or temporal duration of vacuum suction based on the monitored RF current.

Reference is made herein to the evacuation of smoke and components that facilitate such function. It will be appreciated that references to "smoke" is merely for simplicity and convenience, and is not intended to limit the disclosed and claimed embodiments to evacuation of only smoke. Rather, the disclosed and claimed embodiments may be used to evacuate substantially any type of fluid, including liquids, gases, vapors, smoke, or combinations thereof. Additionally, rather than simply evacuating fluid, it is contemplated that at least some of the embodiments may be used to deliver fluids to a desired location, such as a surgical site. As used herein, the term "fluid" includes bulk liquids and/or liquid vapor, which can include liquids—biologic in origin or otherwise—obtained from or introduced into a surgical site (e.g., water, saline, lymph, blood, exudate, pyogenic discharge, and/or other fluid). A "fluid" is additionally intended to include cellular matter or debris that is transported through a vacuum hose and into the fluid reservoir of a mechanically coupled fluid trap.

Current smoke evacuation devices are inefficient and unresponsive to user interaction with components of electrosurgical systems. For example, current smoke evacuation devices are typically turned on or activated before the electrosurgical procedure begins, and the smoke evacuation device is left running for the duration of the electrosurgical procedure. In doing so, any smoke generated during the procedure can be captured and collected from the surgical site and conveyed to the smoke evacuation device for filtering and processing. However, smoke is not continually generated, leaving the smoke evacuation device to convey and filter/process environmental air during non-smoke-generating periods.

In some instances, the smoke filter associated with the smoke evacuation device is monitored for a total number of hours used. That is, the total amount of time the smoke evacuation device is on and providing suction—and therefore pulling air through the smoke filter—is the determinative factor for calculating the life span of the smoke filter, regardless of how many hours the smoke filter was actually being used to filter smoke. Even if the smoke filter was processing relatively clean environmental air for 90% of its temporal life span and would otherwise be deemed clean/useable, many regulations and protocols require the smoke filter to be replaced after so many hours of use. These precautions are intended to guard against the use of clogged or dirty filters, but in practice, it typically results in a tremendous amount of product waste, increased costs, and other inefficiencies within electrosurgical systems.

Additionally, most smoke evacuation devices are not responsive to the variable amount of smoke that can be created throughout an electrosurgical procedure. For example, a great deal of smoke may be generated at various interspersed times during the procedure such as when first cutting tissue at the surgical site or during excision or repair of tissue, whereas at other times, there may be little or no smoke generated such as when the surgeon is performing small delicate incisions or when the surgeon is not using the electrosurgical instrument at all. Regardless of the smoke generation, the smoke evacuation device is likely to be providing constant suction.

In some embodiments, the amount of suction can be manually adjusted, but doing so may detract from the task at hand and can be burdensome to continually monitor and adjust. Further, it may be the case that by the time the user realizes that additional suction is required due to an increased production of smoke, it is likely too late. By the time the suction is adjusted, the smoke will have likely dissipated, making it difficult—if not impossible—to adequately capture and convey to the smoke evacuation device.

One or more embodiments disclosed herein beneficially enable the detection of electrical current within an electrosurgical system and initiate a corresponding activation or modulation of vacuum suction at the smoke evacuation device. Additionally, in some embodiments, a treatment power is derived from the detected current, and based on the derived treatment power, the smoke evacuation device is activated for a defined duration and/or at a defined smoke evacuation flow rate. In some embodiments, the derived treatment power is used to calculate an estimated smoke production, and the smoke evacuation device is activated for a defined duration and/or at a defined smoke evacuation flow rate based on the estimated smoke production.

In some embodiments, an RF current sensor is configured to operate in at least two modes—a first mode and a second mode—and includes a sensor body having at least a cable interfacing sidewall and a retaining member. The cable interfacing sidewall and the retaining member define a retention pocket configured to receive a cable communicating RF current. The RF current sensor additionally includes a sensor element for detecting RF current in the cable and a sensor cable in electrical communication with the sensor element. The sensor cable communicates one or more of an activation signal or a current signal derived from the detected RF current to the smoke evacuation device.

In some embodiments, a method for remote activation of a smoke evacuation device includes generating an RF current at a signal generator, communicating the RF current through a source cable to an electrosurgical instrument, detecting an activation of RF current with an RF current sensor communicatively coupled to a smoke evacuation device, communicating an activation signal from the RF current sensor to the smoke evacuation device in response to detecting the activation of RF current, receiving the activation signal at the smoke evacuation device, and activating a vacuum source for one or more of a defined period of time or to generate a defined smoke evacuation flow rate in response to receiving the activation signal.

In some embodiments, an electrosurgical system includes a signal generator producing an RF current, a source cable electrically coupled to the signal generator and to an electrosurgical instrument, the source cable communicating the RF current from the signal generator to the electrosurgical instrument, a smoke evacuation device that includes a vacuum hose positioned proximate the electrosurgical instrument and configured to evacuate smoke generated by the electrosurgical instrument, and an RF current sensor communicatively coupled to the smoke evacuation device, the RF current sensor activating the smoke evacuation device in response to identifying the RF current.

Such foregoing embodiments of the present disclosure along with additional, or alternative, embodiments described herein can provide a number of benefits. For example, during an electrosurgical procedure, an electrosurgical instrument can be activated for a variable amount of time and/or for variable durations, and this can directly affect the amount and timing of smoke generated during the electrosurgical procedure. Implementations of the present application beneficially enable an associated smoke evacuation device to be activated in response to activation of the electrosurgical instrument and concomitant smoke generation instead of being run constantly. This will reduce the overall time the smoke evacuation device is activated during individual procedures and thereby provide energy savings and increase the life of the smoke evacuation device and/or its components. For example, smoke filters associated with the smoke evacuation device can benefit from an increased life span and/or be more efficiently used by predominantly filtering smoke instead of passively filtering air from a constantly running smoke evacuation device.

In another example, the ability to detect current activation, intensity, and/or duration allows implementations of the present disclosure to adjust the flow rate to accommodate an estimated increase or decrease in smoke generation, thereby providing automatic, dynamic, and responsive smoke evacuation without burdensome oversight, monitoring, or manual adjustments. This can beneficially reduce any visibility reduction, odor, and other problems associated with smoke generation. In some instances, this can enable electrosurgical procedures that generate greater amounts of smoke to be performed or to be performed with less ancillary equipment (e.g., less additional independent vacuum hoses, fans, and other air management equipment) as it can dynamically respond to the smoke generated during the electrosurgical procedure.

Figure 2:
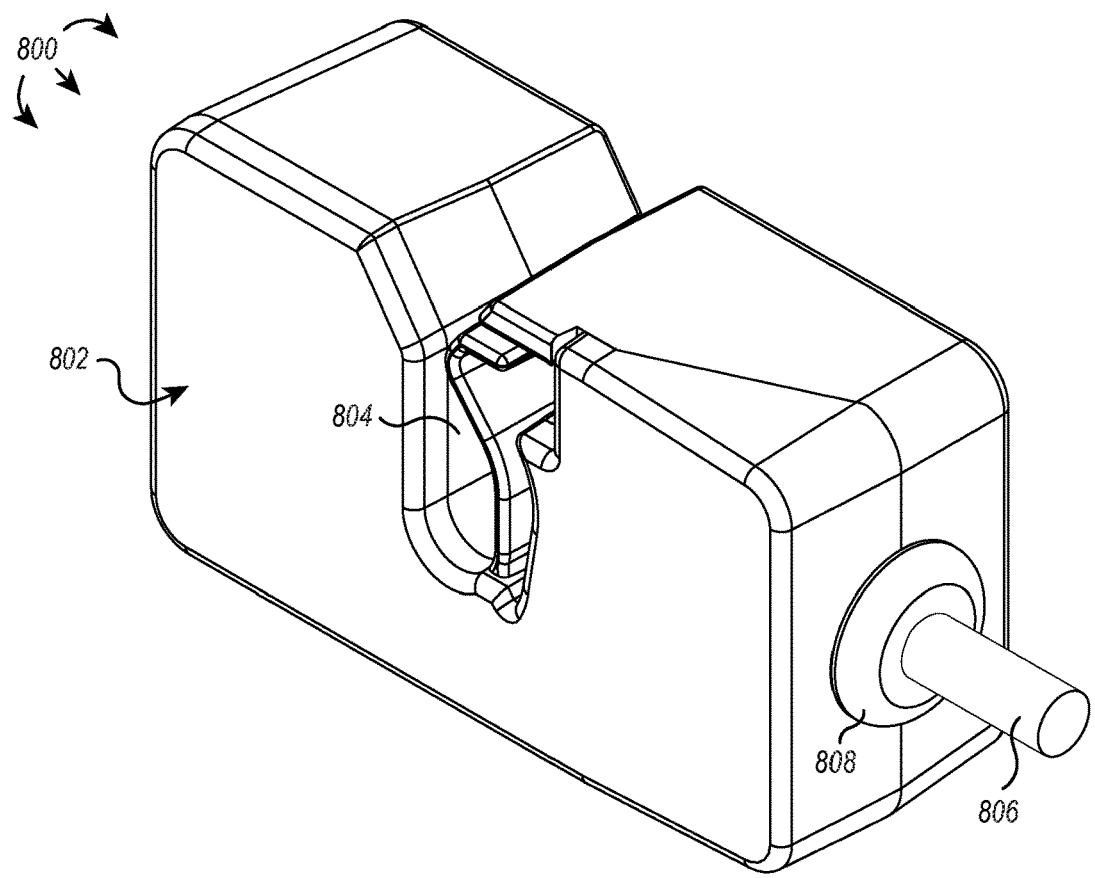
FIG. 2 illustrates a perspective view of an exemplary remote activation clip.
Figure 3:
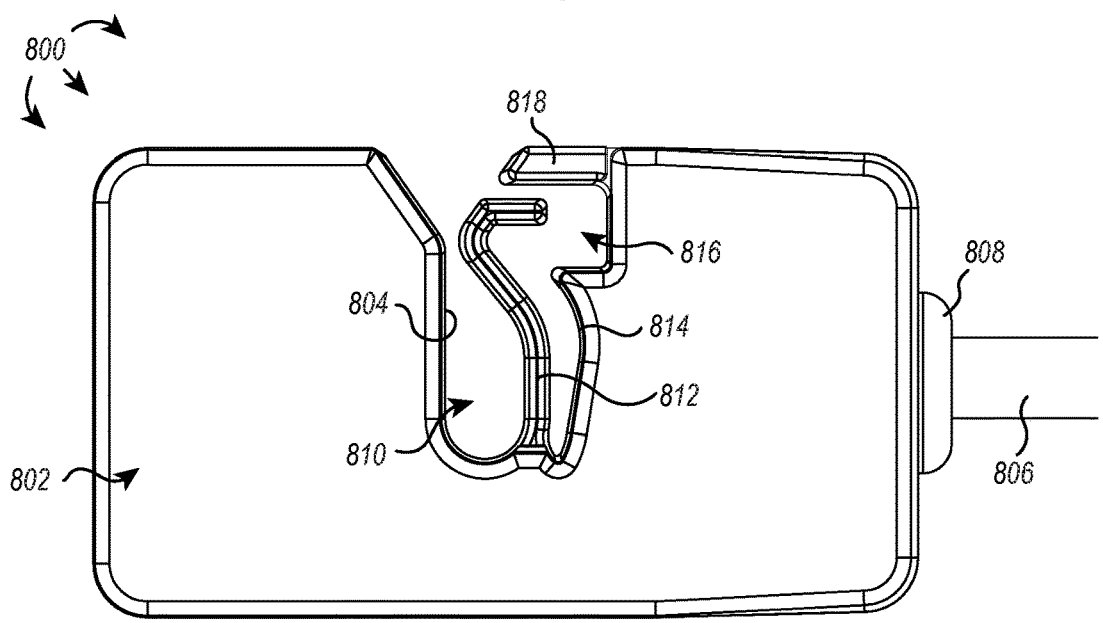
FIG. 3 illustrates an elevation view of the exemplary remote activation clip of FIG. 2.

Referring now to FIGS. 2 and 3, illustrated are perspective and elevation views, respectively, of an exemplary RF current sensor 800. As shown, the RF current sensor 800 includes a sensor body 802 defining most of the visible exterior surfaces of the RF current sensor 800. The RF sensor 800 is associated with a sensor cable 806 at a first end thereof and is retained in place or coupled to the RF sensor 800 by grommet 808. Although depicted as being disposed on a short side of the RF current sensor 800, in some embodiments, the grommet 808 and/or the sensor cable 806 can be disposed on/through any front, side, top, or bottom surface of the RF current sensor 800.

As perhaps best shown in FIG. 3, the sensor body 802 includes a cable interfacing sidewall 804 that at least partially defines a retention pocket 810. The retention pocket is also at least partially defined by the retaining member 812. The retaining member 812 is configured to flex or bend, and in some embodiments—and as illustrated in FIGS. 2 and 3—the RF current sensor 800 can be shaped to accommodate the bending or flexing of the retaining member 812. For example, the sensor body 802 includes a recess sidewall 814 that together with the retaining member 812 and protruding ridge 818 at least partially define a recess 816 into which the retaining member 812 can bend or flex.

The retaining member 812 is illustrated as having a substantially linear lower body that is substantially parallel with the opposing cable interfacing sidewall 804 followed by an arcuate upper body that initially creates a concavity directed towards the retention pocket 810 and narrowing the distance between the cable interfacing sidewall 804 and the retaining member 812. The narrowed distance can serve to prevent unintentional attachment of the RF current sensor 800 to other objects and can also serve to prevent the RF current sensor 800 from unintentionally detaching from an object (e.g., a cable) disposed within the retention pocket 810.

In some embodiments, the retaining member 812 can be biased or flexed towards the recess sidewall 814 and/or into the recess 816, widening the distance between the upper body of the retaining member 812 and the cable interfacing sidewall 804. By doing so, an object can be passed into the retention pocket 810, wherein upon release of the flexed retaining member 812, the object is secured within the retention pocket 810 (e.g., the retaining member 812 mechanically blocks egress of the object from the retention pocket 810).

Additionally, the protruding ridge 818 alone, or in combination with the stop member 815 running substantially parallel thereto, can act to prevent unintentional insertion of an object within the recess 816, which could prevent the retaining member 812 from flexing into the recess 816. Additionally, the length of the stop member 815 and/or the corresponding depth of the recess 816 can act to autoregulate the diameter of cable that can be inserted into the retention pocket 810. For example, a shorter stop member (assuming the same recess 816 depth) will allow the retaining member to flex more, widening the opening and allowing larger diameter cables to enter the retention pocket 810. On the other hand, a longer stop member (again assuming the same recess 816 depth) will prevent the retaining member from flexing and provide a narrower opening through which only smaller diameter cables can pass and enter the retention pocket 810. It should be appreciated that the depth of the corresponding recess 816 can similarly affect the diameter of cable that may enter the retention pocket 810. For example, a deeper recess (assuming the same stop member 815) will allow the retaining member to flex more, widening the opening and allowing larger diameter cables to enter the retention pocket 810 while a shallower recess (again assuming the same stop member 815) will prevent the retaining member from flexing and provide a narrower opening through which only smaller diameter cables can pass and enter the retention pocket 810.

In some embodiments, the stop member 815 and/or the recess 816 are sized to allow a source cable 110 or a return cable 118 to enter the retention pocket 810. Additionally, or alternatively, the stop member 815 and/or the recess 816 are sized to prevent admission of other cables into the retention pocket 810, such as a power cable for the generator 102 or a power cable for the smoke evacuation device 120 or to prevent admission of cable-like objects such as the vacuum hose 112.

The length and configuration of the retaining member 812 and stop member 815 with respect to other features of the RF current sensor 800 can provide additional benefits. For example, the retaining member 812 is contained within the six spatial planes that define the generally box-shaped RF current sensor 800 (e.g., as shown in FIG. 2). That is, the retaining member 812 does not extend or protrude in any direction outside of body of the RF current sensor 800, and this configuration beneficially protects the retaining member from catching on other cables, which could break the retaining member 812. This configuration also protects the retaining member 812 from impact damage if the RF current sensor 800 is dropped or stepped on. Further, because the retaining member 812 is not confluent with any of the six structural sidewalls that make up the box-like dimensions of the RF current sensor 800, it is protected from breakage resulting from a forceful extraction or insertion of a cable into the retention pocket. Additionally, the hard stop relationship between the stop member 812 and the recess 815 allow elastic deformations to the retaining member 812 while preventing plastic deformations or fracturing.

It should be appreciated that the retaining member 812 should not be limited to the exemplary illustration provided in FIGS. 2 and 3. Rather, in some embodiments, the retaining member can include any type or combination of geometries and spatial association with the cable interfacing sidewall. As a non-limiting example, the retaining member can include a horizontal member that encloses the retention pocket similar in form and function to a lid or latch. Additionally, the recess and/or protruding ridge may be omitted, in some embodiments—such as in the foregoing example. It should be noted, however, that embodiments including a horizontal member or that remove the horizontal member or the stop member may not benefit from all of the aforementioned advantages afforded to retaining member 812 of FIG. 3.

In some embodiments, the object retained within the retention pocket 810 is a cable. The cable can be any cable but preferably, the cable includes a source cable 110 or a return cable 118 associated with an electrosurgical system. The cable can serve as a conduit for transmitting RF current from a signal generator 102 to an electrosurgical instrument 104. In the case of a bipolar electrosurgical instrument, the cable can serve as both a source cable and a return cable. In the case of a monopolar electrosurgical instrument, the cable can be one or both of the source cable 110 electrically coupled between the signal generator 102 and the electrosurgical instrument 104 or the return cable 118 electrically coupled between the return electrode 106 and the signal generator 102.

Figure 4:
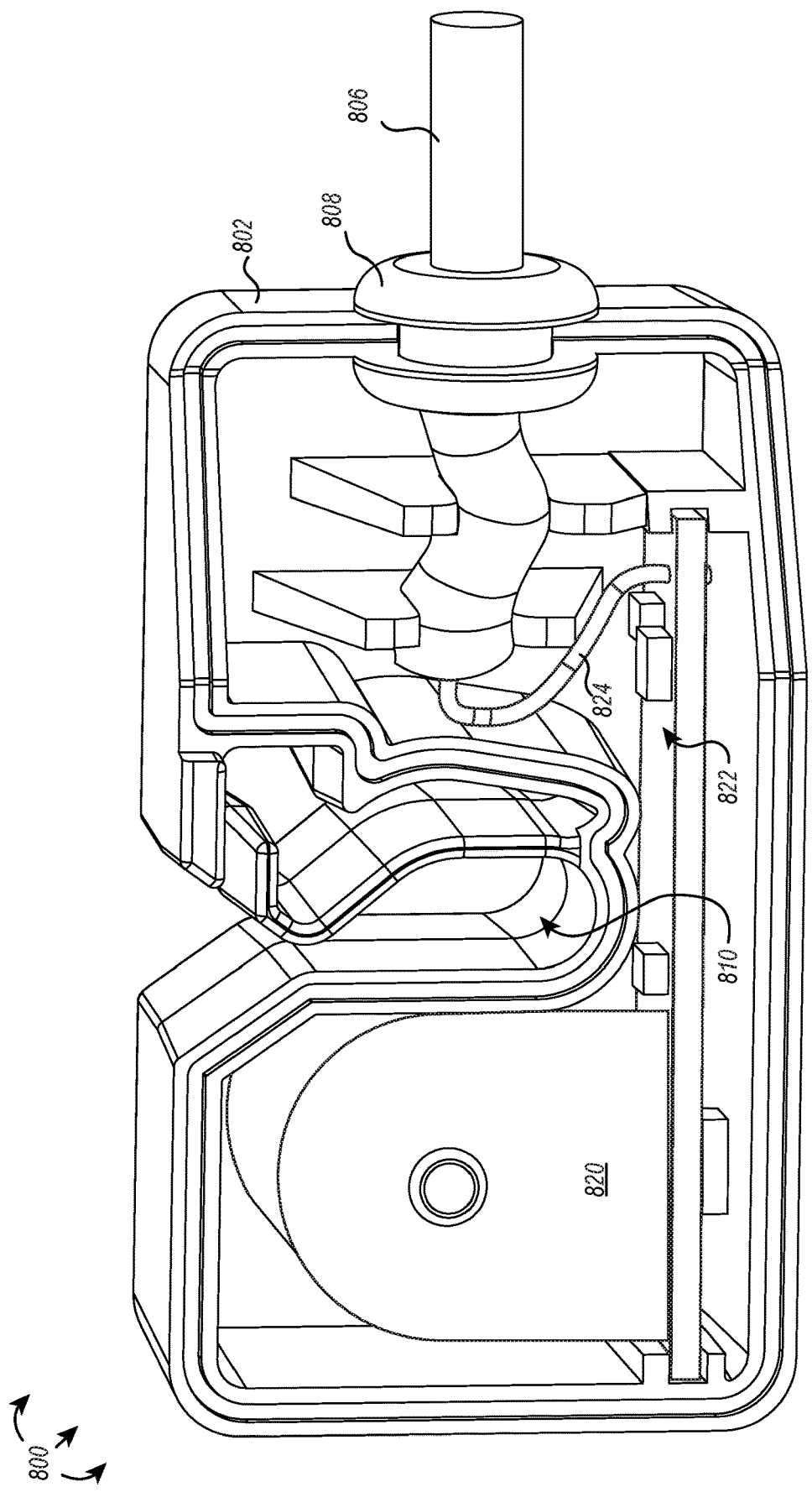
FIG. 4 illustrates a partial cross-sectional view of the exemplary remote activation clip of FIG. 2.

When the cable is disposed within the retention pocket 810, the RF current sensor 800 can detect activation of the RF current through the cable and/or the RF current passing through the cable. In some embodiments, and as shown in FIG. 4, the RF current sensor 800 can include a sensor element 820 housed within the sensor body 802 that detects the activation and/or current of the RF current passing through the cable retained within the retention pocket 810. The sensor element 820 can be any sensor that can detect current within the cable, including, for example, an RF current sensor.

In some embodiments, it may be difficult to detect activation of RF current and/or RF current with a single pass of the cable through the retention pocket 810. In a monopolar system, the RF current signal from the cable can be amplified by looping the cable multiple times through the retention pocket 810. In a bipolar system, the RF current signal can be amplified by separating the source and return strands and looping one of the source or return strands—but not the other—multiple times through the retention pocket 810.

Additionally, or alternatively, it may be advantageous for the sensor element to register detection of RF current above a lower or baseline threshold. For example, a cable may include a low base level of current passing therethrough, even when the electrosurgical instrument is not being used, which could give a false positive indication of RF current passing therethrough. In some embodiments, the baseline threshold is at least 1 mA, at least 5 mA, at least 10 mA, at least 25 mA, at least 50 mA, at least 75 mA, at least 100 mA, at least 150 mA, at least 200 mA, at least 300 mA, at least 400 mA, at least 500 mA, at least 600 mA, at least 700 mA, at least 800 mA, or at least 900 mA.

In addition to the sensor element 820, the sensor body 802 can house various additional internal components of the sensor 800. For example, as illustrated in FIG. 4, the RF current sensor 800 can include a printed circuit board (or similar electronic medium) in electrical communication with the sensor element 820 and which is also in electrical communication with a lead 824. The lead 824 can, in some embodiments, transmit analog data detected and transmitted by the sensor element 820. Additionally, or alternatively, the lead 824 can transmit digital data representative of the signal data (e.g., an activation signal and/or a current signal) detected by the sensor element 820.

In some embodiments, the sensor cable 806 communicates an activation signal or a current signal derived from the detected RF current to a smoke evacuation device. When received by the smoke evacuation device, the activation signal and/or current signal, can cause a vacuum source to be activated for a period of time and/or cause the vacuum source to generate a defined smoke evacuation flow rate. In some embodiments, the activation signal and/or the current signal are proportional to the detected RF current and thereby cause an effect at the smoke evacuation device that is commensurate with the detected signal.

For example, if the RF current sensor detects activation of the RF current, the sensor cable can communicate instructions to the smoke evacuation device to turn on the vacuum system to a low setting. If the RF current sensor fails to detect RF current thereafter, the sensor cable can communicate instructions to the smoke evacuation device to deactivate the vacuum system. In some embodiments, the deactivation is immediate. In other embodiments, the vacuum system runs for a defined period of time to ensure capture and conveyance of any smoke generated at the surgical site. It should be appreciated that the sensor cable can communicate any pre-defined (e.g., turn vacuum system on high) or user-defined instruction in response to the RF current sensor detecting activation of the RF current through the associated cable.

As an additional example, the if the RF current sensor detects activation of the RF current followed by sustained RF current, the sensor cable can communicate instructions to the smoke evacuation device to create a high smoke evacuation flow rate (e.g., by turning the vacuum system on its highest setting).

In some embodiments, the sensor cable 806 is physically coupled to the RF current sensor 800 and can electrically communicate with the RF current sensor 800 and the smoke evacuation device 120. In some embodiments, the sensor cable 806 is also physically coupled to the smoke evacuation device 120. In yet other embodiments, the sensor cable communicates wirelessly with the smoke evacuation device.

Figure 5:
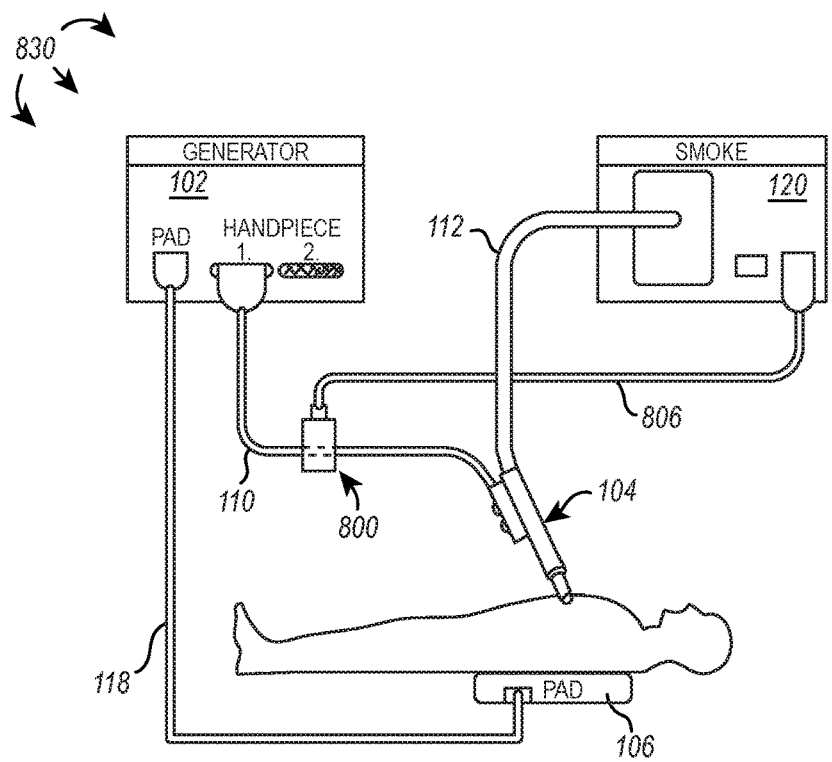
FIG. 5 illustrates a remote activation clip associated with a cable leading to the electrosurgical instrument of the depicted electrosurgical system.

As provided above, the RF current sensor 800 can, in some embodiments, selectively clip onto a source cable 110 and/or a return cable 118 and be retained thereon, detecting RF activation events and/or RF current through the cable 110, 118. For example, as illustrated in FIG. 5, an electrosurgical system 830 can include a signal generator 102 that generates an RF current and communicates the RF current to an electrosurgical instrument 104 (illustrated as a monopolar electrosurgical instrument) through a source cable 110. The RF current is transmitted through the patient and received at the return electrode 106, completing the circuit to the signal generator 102 through return cable 118. As illustrated, a vacuum hose 112 extends from the smoke evacuation device 120 to the surgical site proximate the electrosurgical instrument 104 and is positioned to extract smoke generated by the electrosurgical instrument 104 and convey the smoke to the smoke evacuation device 120 for filtering/processing.

The electrosurgical system 830 additionally includes an RF current sensor 800 removably associated with the source cable 110 and connected to the smoke evacuation device 120 by sensor cable 806. The RF current sensor 800 can detect an activation of RF current passing through the source cable 110, and in response to detecting the activation of RF current, the RF current sensor 800 can communicate an activation signal to the smoke evacuation device 120. In response to receiving the activation signal, the smoke evacuation device 120 can activate a vacuum source for a defined period of time or to generate a defined smoke evacuation flow rate. In some embodiments, the defined period of time or the defined smoke evacuation flow rate is proportional to the activation signal or a plurality of previously detected activation signals. For example, if the RF current sensor 800 detects a series of RF activation events in close temporal proximity, the RF current sensor 800 can instruct the smoke evacuation device 120 to activate the vacuum system for a prolonged period of time, as the plurality of detected activation signals can be indicative of successive electrosurgical events that can in the aggregate generate sufficient smoke to warrant prolonged smoke evacuation.

It should be appreciated that the RF current sensor 800 can additionally, or alternatively, detect RF current through source cable 110 and communicate instructions to the smoke evacuation device 120 in a similar fashion as described above.

Figure 6:
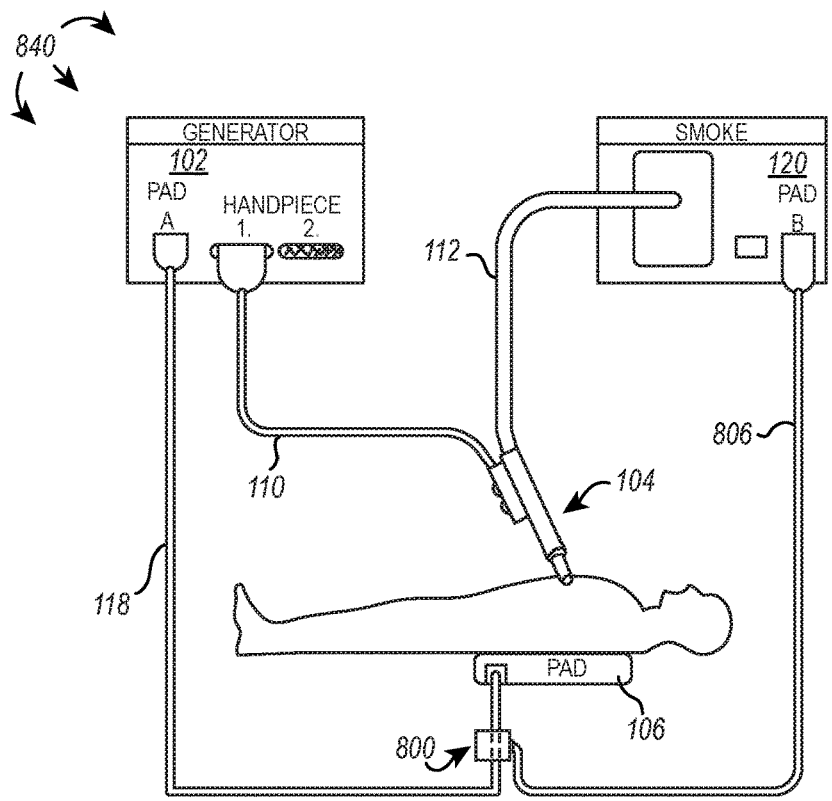
FIG. 6 illustrates a remote activation clip associated with a cable extending from the return electrode of the depicted electrosurgical system.

As shown in FIG. 6, an electrosurgical system 840 can include a similar setup as described above with respect to electrosurgical system 830. That is, an electrical circuit for transmitting RF current can be formed from the signal generator 102, to a source cable 110, electrosurgical instrument 104, return electrode 106, and return cable 118, completing the electrical circuit at the signal generator 102. Instead of the RF current sensor 800 being positioned on the source cable 110, as described above with respect to FIG. 5, the RF current sensor 800 is removably attached to the return cable 118. However, similar to the RF current sensor 800 of FIG. 5, the RF current sensor 800 of FIG. 6 is connected to the smoke evacuation device 120 by sensor cable 806.

The RF current sensor 800 of FIG. 6 can detect an activation of RF current passing through the return cable 118, and in response to detecting the activation of RF current, the RF current sensor 800 can communicate an activation signal to the smoke evacuation device 120. Similarly, it should be appreciated that the RF current sensor 800 can additionally, or alternatively, detect RF current through return cable 118 and communicate instructions to the smoke evacuation device 120 in a similar fashion as described above.

Figure 7:
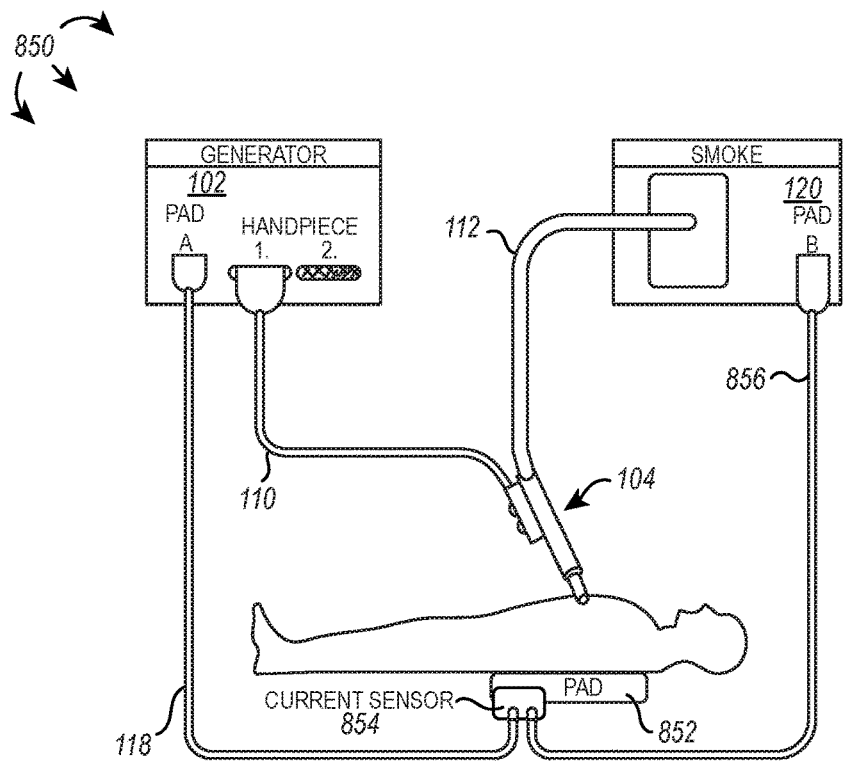
FIG. 7 illustrates a current sensor associated with the return electrode of the depicted electrosurgical system.

As shown in FIG. 7, an electrosurgical system 850 can include a similar setup as described above with respect to electrosurgical systems 830 and 840. That is, an electrical circuit for transmitting RF current can be formed from the signal generator 102, to a source cable 110, electrosurgical instrument 104, return electrode 852, and return cable 118, completing the electrical circuit at the signal generator 102. However, instead of the RF current sensor 800 being releasably connected to the source cable 110 (as in FIG. 5) or to the return cable 118 (as in FIG. 6), the RF current sensor 854 is integrally formed within the return electrode 852. The return electrode 852 includes pigtails or other electrical outlets that electrically couple the return electrode 852 to the signal generator 102, thereby completing the circuit, and also allow electrical coupling of the return electrode 852 with the smoke evacuation device 120 through a sensor cable 856.

The RF current sensor 854 within the return electrode 852 detects RF current activation as the RF current is received and passes through the return electrode 852. Additionally, the RF current sensor 854 can detect RF current passing through return electrode 852. In response to the current sensor 854 detecting RF current activation and/or the RF current passing through the return electrode 852, the current sensor 854 can communicate with the smoke evacuation device 120 to activate and modulate smoke evacuation flow rate and/or a period of time the smoke evacuation device 120 is activated, as described herein.

Figure 8:
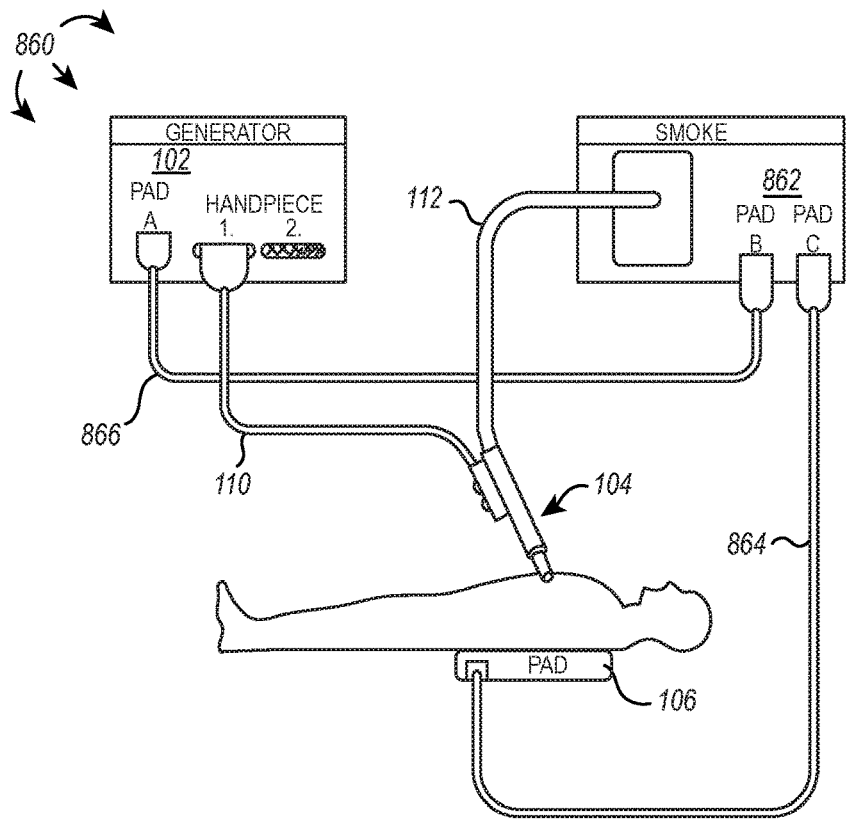
FIG. 8 illustrates a current sensor associated with the smoke evacuation device of the depicted electrosurgical system.

In some embodiments, and as illustrated in FIG. 8, a smoke evacuation device 662 can include an RF current sensor integrally formed therein. In the electrosurgical system 860 incorporating the smoke evacuation device 862, a signal generator 102 can generate an RF current and communicate the RF current to an electrosurgical instrument 104 (again illustrated as a monopolar electrosurgical instrument) through the resource cable 110. The RF current is transmitted through the patient and received at the return electrode 106 and completes the circuit to the signal generator 102 by passing through the smoke evacuation device 862 along a series of return cables 864, 866. More particularly, the RF current is passed between the return electrode 106 and the smoke evacuation device 862 via first return cable 864, and the RF current is passed between the smoke evacuation device 862 and the signal generator 102 via second return cable 866. As the RF current passes through the smoke evacuation device 862, the integrally formed RF current sensor can detect one or both of an RF activation event or RF current passing therethrough. Upon detecting activation of RF current and/or RF current passing through the smoke evacuation device 862, the integrally formed RF current sensor can communicate directly or indirectly with the vacuum system to activate and/or modulate airflow into the smoke evacuation device for a defined or dynamic period of time.

Figure 9:
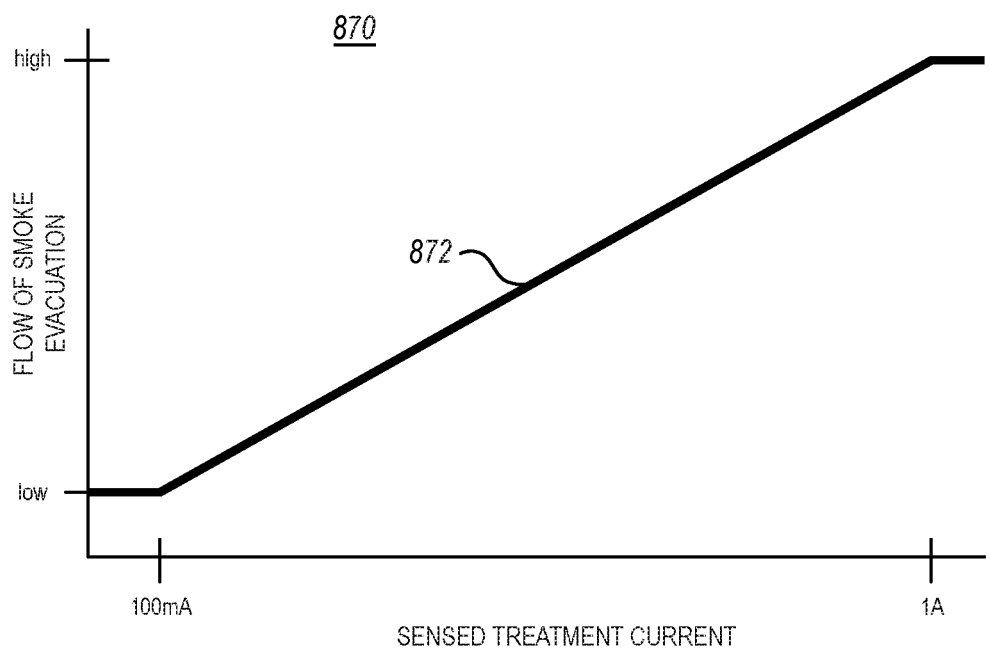
FIG. 9 illustrates an exemplary graph depicting a potential smoke evacuation flow rate with respect to the sensed treatment current from current sensors described herein.

In some embodiments, the RF current sensor can dynamically adjust the smoke evacuation flow rate in response to a sensed treatment current. For example, as shown in the graph 870 illustrated in FIG. 9, the smoke evacuation flow rate can be dynamically adjusted based on the current detected by the RF current sensor. As the current increases, the flow rate increases, and as the current decreases, the flow rate decreases.

It should be appreciated that although graph 870 illustrates a smoke evacuation curve 872 having a linear relationship between the sensed treatment current in the smoke evacuation flow rate, other relationships are possible. For example, the smoke evacuation flow rate may increase logarithmically or exponentially with respect to a sensed treatment current. In some embodiments, it may be advantageous to increase the smoke evacuation flow rate rapidly at the lower end of the sensed treatment current to ensure that any smoke generated at the surgical site has sufficient suction port extraction and conveyance to the smoke evacuation device.

In some embodiments, it may be advantageous to increase the smoke evacuation flow rate slowly at the lower end of the sensed treatment current within a rapid increase in the smoke evacuation flow rate before, at, or after the predefined treatment current or smoke generation is known to occur. In doing so, the smoke evacuation device is not activated until smoke is presumed to be generated, thereby preserving the life of the smoke evacuation device or components thereof, such as the smoke filter.

Figure 10:
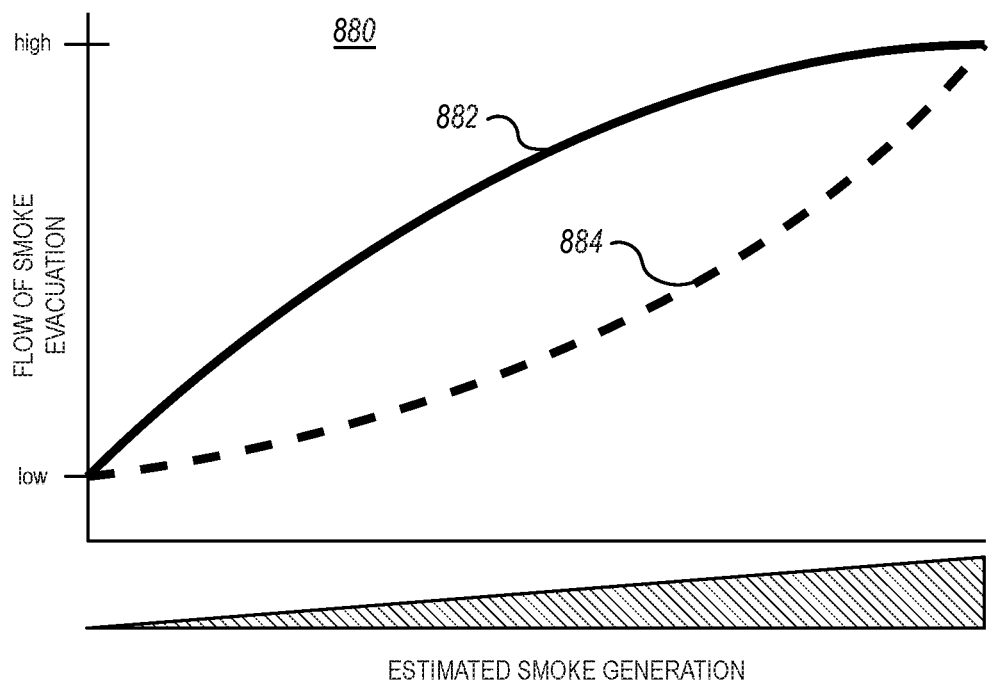
FIG. 10 illustrates an exemplary graph depicting potential smoke evacuation flow rates with respect to an estimated amount or volume of generated smoke.

In some embodiments, the detected current can be used to derive an estimate of the treatment power delivered to tissue, and in turn, the estimated treatment power delivered to tissue can be correlated with a tissue effect and the smoke generated as a result of such a tissue effect. Accordingly, in some embodiments, the detected current can be used to infer an estimated amount or volume of smoke, and that information can be used to dynamically adjust the smoke evacuation flow rate. For example, as illustrated in the graph 880 of FIG. 10, an amount or volume of estimated smoke generation can be derived based on the detected current, and the smoke evacuation flow rate can be adjusted accordingly.

In one embodiment, and as represented by the first smoke evacuation curve 882, the smoke evacuation flow rate can correlate with an estimated smoke generation in a logarithmic fashion. In another embodiment, and as represented by the second smoke evacuation curve 884, smoke evacuation flow rate can correlate with an estimated smoke generation in a polynomial or exponential fashion. In some embodiments, the smoke evacuation flow rate can correlate with an estimated smoke generation linearly (not shown).

Thus, implementations of the present disclosure enable a smoke evacuation flow rate to be dynamically modified in a way that is proportional to and/or dependent upon the current detected by the current sensor. In some embodiments, however, the direct correlation between the detected current in the smoke evacuation flow rate may not be optimal. For example, different currents may affect tissue differently and thereby cause differential smoke production that is difficult to account for when only correlating the detected current and the smoke evacuation flow rate. Furthermore, continued exposure to single or different currents may result in a smoke plume that would be unaccounted for when only correlating the detected current in the smoke evacuation flow rate.

Accordingly, implementations of the present disclosure further enable a smoke evacuation flow rate to be dynamically modified in a way that is proportional to and/or dependent upon a tissue effect and resulting smoke generation that is caused by a given treatment power. In some embodiments, the energy associated with an activation of RF current can be estimated by multiplying the treatment power by the activation time. The estimated energy can be correlated with an amount or volume of smoke produced from exposure to the estimated energy, and the smoke evacuation flow rate can be adjusted based on this amount or volume of smoke.

Similarly, the energy associated with a plurality of activations of RF current and/or energy associated with continuous RF current can be estimated by multiplying the treatment power by the activation time for each activation of RF current and/or exposure to continuous RF current. The total estimated energy can be correlated with an amount or volume of smoke produced from exposure to the total estimated energy, and the smoke evacuation flow rate can be adjusted based on this amount or volume of smoke.

While the embodiments described herein have been directed to electrosurgical instruments with smoke evacuation features, the present disclosure is not intended to be so limited. Rather, the present disclosure is broadly directed to any hand-held instrument that includes fluid (e.g., liquids, gases, vapors, smoke, or combinations thereof) evacuation or delivery features as described herein. By way of non-limiting example, such hand-held instruments may include dental instruments (e.g., drills, polishing tools, scalers, compressed air tools, suction tools, irrigation tools, carries detection tools, water flossing tool (e.g., waterpik)), soldering tools (e.g., heated tools, smoke collection tools, desoldering tools), high speed grinding and polishing tools (e.g., Dremel tools, carving tools, manicure tools, dental lab grinders/polishers), laser treatment instruments, laser surgical instruments, light probes, suction handles (e.g., Yankauer), blasting tools (e.g., sandblast, gritblast), shockwave therapy tools, ultrasonic therapy tools, ultrasonic probe tools, ultrasonic surgical tools, adhesive application instruments, glue guns, pneumatic pipettes, welding tools, RF wrinkle therapy hand pieces, phaco hand pieces, shears, shaver, or razor hand pieces, micro drill hand pieces, vacuum hand pieces, small parts handling hand pieces, tattoo needle handles, small torch hand pieces, electrology hand pieces, low speed grinding, polishing and carving tools, permanent makeup hand pieces, electrical probe hand pieces, ferromagnetic surgical hand pieces, surgical plasma hand pieces, argon beam surgical hand pieces, surgical laser hand pieces, surgical suction instruments (e.g., liposuction cannulas), surgical suction cannulas, microdermabrasion hand pieces, fiberoptic camera handles, microcamera hand pieces, pH probe hand pieces, fiberoptic and LED light source hand pieces, hydrosurgery hand pieces, orthopedic shaver, cutter, burr hand pieces, wood burning tools, electric screwdrivers, electronic pad styluses, and the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A radio frequency (RF) system, comprising:
   an RF current sensor configured for remotely activating a smoke evacuation device in an electrosurgical system, the RF current sensor comprising:
      a sensor body comprising a cable interfacing sidewall, a recess sidewall opposite the cable interfacing sidewall, and a lower sidewall that extends between the cable interfacing sidewall and the recess sidewall, the sensor body further comprising a retaining member integrally formed with or permanently connected to the lower sidewall and extending therefrom between the cable interfacing sidewall and the recess interfacing sidewall, the cable interfacing sidewall and the retaining member defining a retention pocket configured to receive a cable that is configured to communicate RF current;
      a sensor element configured for detecting RF current in the cable; and
      a sensor cable in electrical communication with the sensor element, the sensor cable being configured to communicate one or more of an activation signal or a current signal derived from the detected RF current to the smoke evacuation device,
      wherein the RF current sensor is configured to operate in at least two modes: a first mode and a second mode.

2. The radio frequency (RF) system as in claim 1, wherein the retaining member is configured to flex away from the cable interfacing sidewall and towards the recess sidewall to admit the cable into the retention pocket.

3. The radio frequency (RF) system as in claim 2, wherein the recess sidewall comprises a recess formed therein, the recess in the recess sidewall being configured to selectively receive a free end of the retaining member therein only when the retaining member is flexed away from the cable interfacing sidewall and towards the recess sidewall.

4. The radio frequency (RF) system as in claim 1, wherein:
   the RF current sensor operates in the first mode when the sensor element identifies a single RF current in the cable, the single RF current in the cable being communicated between a signal generator and an active electrode of a monopolar electrosurgical instrument or between a return electrode and the signal generator, and wherein one or more of the activation signal or the current signal are derived from the single RF current when the RF current sensor operates in the first mode, and
   the RF current sensor operates in the second mode when the sensor element identifies two RF currents—a first RF current flowing in an opposite direction as a second RF current—in the cable, wherein the second mode causes the RF current sensor to detect the first RF current with respect to the second RF current, and wherein one or more of the activation signal or the current signal are derived from the first RF current when the RF current sensor operates in the second mode.

5. The radio frequency (RF) system as in claim 1, further comprising an electrosurgical system, the electrosurgical system comprising:
   a signal generator configured to produce RF current;
   a source cable electrically coupled to the signal generator and to an electrosurgical instrument, the source cable being configured to communicate the RF current from the signal generator to the electrosurgical instrument, the source cable being configured to be received within the retention pocket of the sensor body; and a smoke evacuation device comprising a vacuum hose, the vacuum hose being positionable proximate the electrosurgical instrument and configured to evacuate smoke generated by the electrosurgical instrument, wherein the RF current sensor is configured to be communicatively coupled to the smoke evacuation device, the RF current sensor being configured to activate the smoke evacuation device in response to the RF current sensor detecting RF current in the source cable.

6. The radio frequency (RF) system as in claim 5, wherein the RF current sensor is configured to be removably coupled to the source cable.

7. The radio frequency (RF) system as in claim 5, wherein the electrosurgical instrument comprises a monopolar electrosurgical instrument, and wherein the electrosurgical system further comprises a return electrode and a return cable, the return cable being configured to communicate RF current from the return electrode to the signal generator.

8. The radio frequency (RF) system as in claim 7, wherein the RF current sensor is configured to be removably coupled to the return cable, and wherein the RF current sensor is configured to activate the smoke evacuation device after detecting RF current communicated through the return cable.

9. The radio frequency (RF) system as in claim 7, wherein the RF current sensor is configured to detect RF current communicated to the return electrode, and wherein the RF current sensor is configured to communicate a signal through the sensor cable electrically coupled to the return electrode and the smoke evacuation device.

10. The radio frequency (RF) system as in claim 7, wherein the smoke evacuation device is configured to be electrically coupled to the return electrode by a first return cable and to the signal generator by a second return cable, and wherein the RF current sensor is configured to detect RF current communicated from the first return cable to the second return cable.

11. The radio frequency (RF) system as in claim 1, wherein the retaining member has an arcuate portion configured to extend partially around the cable to secure the cable within the retention pocket.

12. The radio frequency (RF) system as in claim 11, wherein the arcuate portion extends towards the cable interfacing sidewall.

13. The radio frequency (RF) system as in claim 1, wherein the sensor body comprises a protruding ridge and/or the retaining member comprises a stop member, the protruding ridge and/or the retaining member being configured to limit unintentional insertion of an object between the retaining member and the recess sidewall.

14. A radio frequency (RF) system, comprising:
an RF current sensor, comprising:
a sensor body comprising a cable interfacing sidewall and a retaining member, the retaining member having a first end that is integrally formed with or permanently connected to the sensor body, the cable interfacing sidewall and the retaining member defining a retention pocket configured to receive a cable that is configured to communicate RF current, the retaining member having a second, free end that is configured to flex away from the cable interfacing sidewall to admit the cable into the retention pocket, and the second, free end of the retaining member having an arcuate portion that extends towards the cable interfacing sidewall and is configured to extend partially around the cable to secure the cable within the retention pocket;

a sensor element configured for detecting RF current in the cable, wherein the RF current sensor is configured to operate in a first mode and a second mode, wherein:
the RF current sensor operates in the first mode when the sensor element identifies a single RF current in the cable; and
the RF current sensor operates in the second mode when the sensor element identifies two RF currents—a first RF current flowing in an opposite direction as a second RF current—in the cable.

15. The radio frequency (RF) system as in claim 14, wherein, in the second mode, the RF current sensor is configured to detect the first RF current with respect to the second RF current.

16. The radio frequency (RF) system as in claim 14, wherein the retaining member is configured to flex about an axis that is parallel to an axis of the cable received within the retention pocket.

17. The radio frequency (RF) system as in claim 14, wherein the sensor body further comprises a recess sidewall opposite the cable interfacing sidewall and towards which the retaining member is configured to flex when the retaining member flexes away from the cable interfacing sidewall.

18. The radio frequency (RF) system as in claim 14, wherein the sensor body comprises a protruding ridge and/or the retaining member comprises a stop member, the protruding ridge and/or the retaining member being configured to limit unintentional insertion of an object between the retaining member and the recess sidewall.

19. A radio frequency (RF) system, comprising:
an RF current sensor configured for remotely activating a smoke evacuation device in an electrosurgical system, the RF current sensor comprising:
a sensor body comprising a cable interfacing sidewall, a recess sidewall opposite the cable interfacing sidewall, a lower sidewall that extends between the cable interfacing sidewall and the recess sidewall, and a retaining member integrally formed with or permanently connected to the lower sidewall and extending therefrom between the cable interfacing sidewall and the recess interfacing sidewall, the cable interfacing sidewall and the retaining member defining a retention pocket configured to receive a cable that is configured to communicate RF current, the retaining member having a first end that is integrally formed with or permanently connected to the lower sidewall and a second, free end that is configured to flex away from the cable interfacing sidewall to admit the cable into the retention pocket, and the second, free end of the retaining member having an arcuate portion that extends towards the cable interfacing sidewall and is configured to extend partially around the cable to secure the cable within the retention pocket;

a sensor element configured for detecting RF current in the cable; and a sensor cable in electrical communication with the sensor element, the sensor cable being configured to communicate one or more of an activation signal or a current signal derived from the detected RF current to the smoke evacuation device, wherein the RF current sensor is configured to operate in at least two modes: a first mode and a second mode.

20. The radio frequency (RF) system as in claim 19, wherein the sensor body comprises a protruding ridge and/or the retaining member comprises a stop member, the protruding ridge and/or the retaining member being configured to limit unintentional insertion of an object between the retaining member and the recess sidewall.

* * * * *